United States Patent [19]

Gott

[11] Patent Number: 4,850,112
[45] Date of Patent: Jul. 25, 1989

[54] FINENESS GAUGE

[75] Inventor: Granville Gott, Chalfont St. Peter, England

[73] Assignee: Imperial Chemical Industries, Great Britain

[21] Appl. No.: 105,023

[22] Filed: Oct. 6, 1987

[30] Foreign Application Priority Data

Nov. 4, 1986 [GB] United Kingdom ................ 8626294

[51] Int. Cl.⁴ .............................................. G01B 5/00
[52] U.S. Cl. ..................................................... 33/501
[58] Field of Search ............. 33/168 R, 169 R, 169 B,
33/169 F, 1 BB, 1 C; 73/61.1 C, 865.5, 150 R

[56]  References Cited

U.S. PATENT DOCUMENTS 2,846,772  8/1958  Strausser ...................... 33/168 R X
3,771,232  11/1973  Specht ........................... 33/168 R X
4,584,774  4/1986  Link ...................................... 33/168 R

FOREIGN PATENT DOCUMENTS 0100601  5/1986  Japan ................................. 33/169 F
1097891  6/1984  U.S.S.R. .......................... 33/169 F Primary Examiner—Harry N. Haroian
Attorney, Agent, or Firm—Cushman, Darby & Cushman

[57]  ABSTRACT

A gauge for determining the fineness of particles dispersed in a liquid comprises a block (1) having a reference surface (8) in which are formed a series of flats (2) at different depths below the surface (8). In use of the gauge the liquid is spread over the surface (8) by a spreader blade resting on and drawn across the surface (8). The fineness of the particles in the liquid is interpreted from the manner in which the liquid has covered the flats (2) under the action of the spreader blade.

11 Claims, 2 Drawing Sheets

FINENESS GAUGE

BACKGROUND OF THE INVENTION

This invention relates to gauges for determining the fineness of particles dispersed in a liquid medium. The invention has particular application in the manufacture of paints for determining the fineness of pigment particles dispersed in a resin base after grinding.

One known gauge for determining the fineness of pigment particles in paints is the Heckmann gauge. This comprises an elongated metal block with a longitudinal groove in its upper surface, the depth of the groove gradually decreasing from one end to the other. In use of this gauge a load of paint is placed at the deep end of the groove and drawn along it by a spreader blade whose knife edge is in contact with the upper surface of the metal block. In this way the paint will be spread along the groove until the depth of the groove is less than the diameter of the pigment particles. The paint will then be scraped along the bottom of the groove by the spreader leaving, so to speak, a cut-off position in the groove. The upper surface of the block is marked with a scale along its length indicating for example the depth of the groove at various positions along it so that the cut-off position can be read off this scale and from this reading the pigment particle size can be interpreted.

One disadvantage of this known gauge is that the cut-off position can not be easily determined, because it is in most cases formed by a jagged line across the groove. Another disadvantage is that with solvent based paints some of the solvent evaporates during the test and so the cut-off position tends to creep back.

The object of the invention is to overcome the aforesaid disadvantages.

SUMMARY OF THE INVENTION

According to the invention there is provided a fineness gauge for assessing the fineness of particles dispersed in a liquid comprising a block having a reference surface which in use is designed to have the liquid spread over it by a spreader resting on and drawn across the reference surface, and wherein there is formed in the reference surface a plurality of flats at different depths below the reference surface.

Preferably the flats are arranged in a sequence, for example a straight line sequence, of increasing depth and may be rectangular or other convenient shape. At least one channel may be formed in the reference surface to a depth greater than that of the deepest flat, an edge portion of each of the flats opening into the channel. Preferably, there are two such channels disposed with the flats between them. Such channels allow excess liquid on the reference surface to flow away when the gauge is in use.

Generally the flats are identified according to their depth below the reference surface. Preferably the flats are identified by an indicium on or adjacent each flat. The indicium may, for example, be in the form of a number which gives the actual depth of each flat. The indicia may be located on the reference surface. Alternatively they may be located on a surface not contacted in use by the spreader blade to reduce the likelihood of their being obscured by liquid during use. Thus the indicia may be located on a surface which slopes away from the reference surface for example as a chamfered edge.

Use of the gauge in accordance with the invention in assessing the fineness of solids in a liquid medium, the gauge having a sequence of flats of increasing depth, comprises the steps of (i) placing a load of the liquid medium before the deepest flat in the sequence, (ii) distributing the liquid along the sequence with a spreader blade by drawing the spreader across the load of paint and along the sequence of flats with its straight edge resting on the reference surface, bridging the flats and (iii) inspecting the film of liquid produced on the flats as to determine the particle size. The solids particle size may be interpreted from the last flat having a wholly coherent film of paint. Alternatively, it may be interpreted from the last flat having for example no more than two breaks in the paint film. As a still further alternative a comparison of the paint films on the flats can be made with a photograph of the paint films produced by a standard paint.

BRIEF DESCRIPTION OF THE DRAWINGS

Constructions of gauge in accordance with the invention will now be described by way of example, with reference to the accompanying drawings, in which.

DETAILED DESCRIPTION

Figure 1:
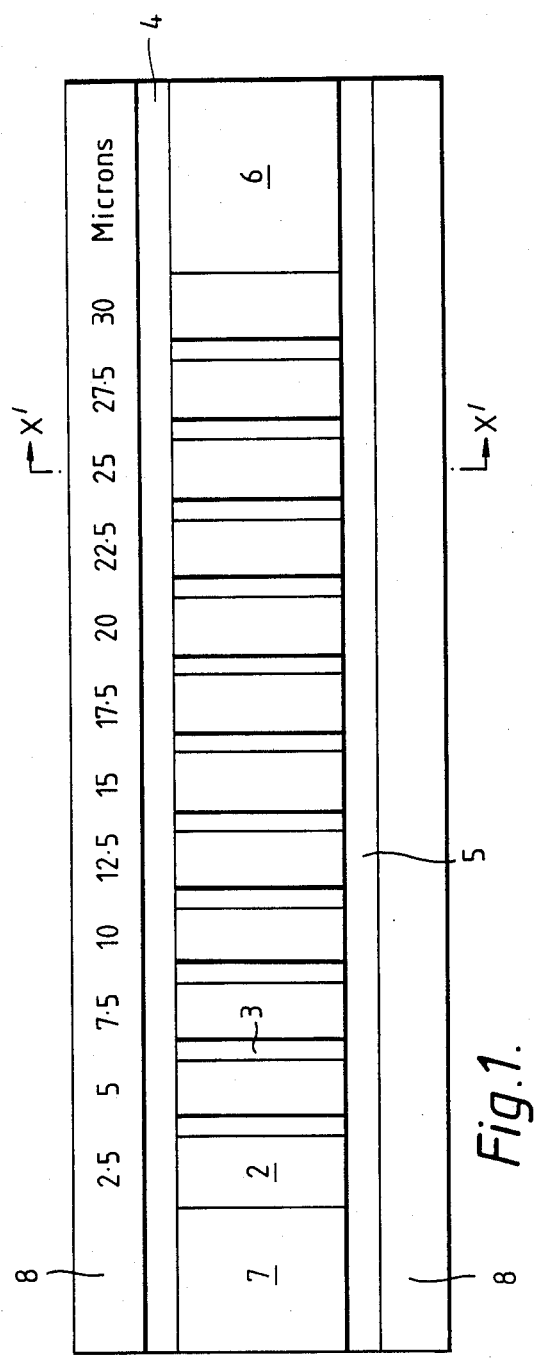
FIG. 1 is a top plan view of a first construction of gauge.
Figure 2:
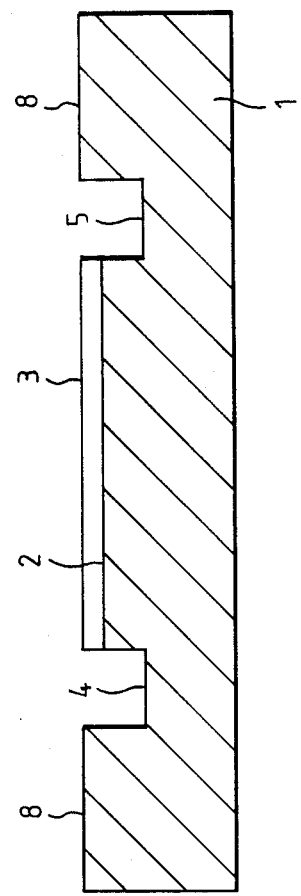
FIG. 2 is an enlarged sectional view on the line X—X' of FIG. 1.

Referring now to FIGS. 1 and 2 of the drawings the first construction of gauge comprises an elongated rectangular steel block 1 having in its upper surface 8 a longitudinal series of discrete rectangular flats 2 forming a straight line sequence. The flats 2 are formed by grinding shallow transverse grooves into the surface of the block and are of increasing depth from one end of the sequence to the other. The flats are separated from each other by narrow bars 3 left after grinding. The ends of the flats are bounded by longitudinal grooves 4 and 5 into which the ends of the flats open. These grooves 4 and 5 assist in grinding of the flats 2 in that they enable the flats 2 to stop short of the sides of the block 1 without having a curvature at the ends of the flats 2. They also provide runways for excess paint.

Each of the flats 2 is given a calibration number. In the drawings the numbers indicate the depths of the flats below the surface of the block 1. Thus the shallowest flat is 2.5 microns and the deepest 60 microns. At either end of the series of flats are lands 6 and 7.

In use of the gauge a load of paint is placed on land 6 in front of the deepest flat 2 and is then drawn along the surface 8 of the block by a spreader blade with its lower knife edge in contact with the surface 8. The blade edge is sufficiently long to extend the whole width of the block. As the paint spreads along the block it will form at each successive flat 2 a thinner film than at the previous one determined by the depth of the flat. Eventually a flat 2 is reached on which the paint will not form a coherent film because the particle size of the pigment is greater than the depth of the flat. As mentioned above the last coherent film can be used to interpret the pigment particle size or predetermined characteristics of incoherent films can be used.

Figure 3:
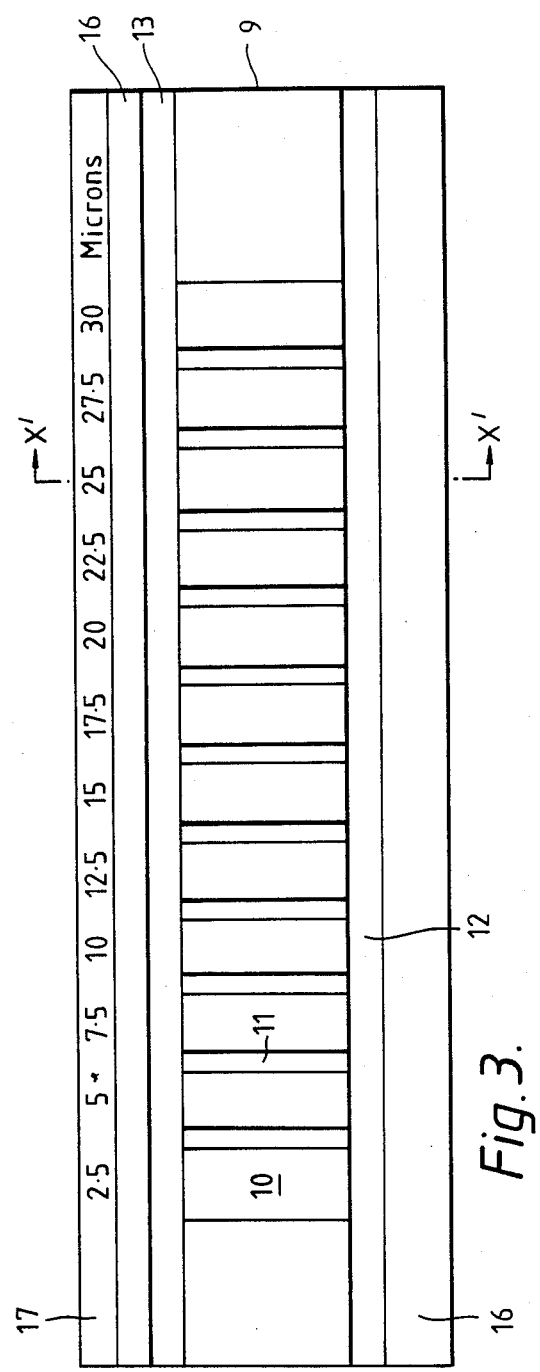
FIG. 3 is a top plan view of a second construction of gauge.
Figure 4:
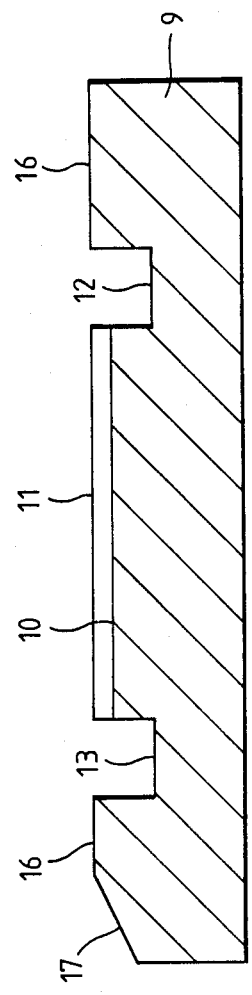
FIG. 4 is an enlarged sectional view on the line X—X' of FIG. 3.

Referring now to FIGS. 3 and 4 the second construction of gauge similar to the first construction comprises an elongated rectangular steel block 9 having a longitudinal series of discrete rectangular flats 10 formed in its upper surface 16. The flats are separated from each other by narrow bars 11. The ends of the flats are bounded by longitudinal grooves 12 and 13.

In contrast to the first construction, there is an indicator surface 17 running the length of the block 9 which is inclined away from the flats 10 as a chamfered edge of the block 9. On this surface are numbers indicating the depth of the flats 10 below the surface 16 of the block. The inclination of this indicator surface reduces the tendency of the numbers to be obscured by paint during use.

The second construction of gauge is used precisely in the same way as the first construction.

I claim:

1. A fineness gauge for assessing the fineness of particles dispersed in a liquid comprising a block having a reference surface, said block being designed to have the liquid to be assessed spread over it with a spreader resting on and drawn across the reference surface, and wherein a plurality of flats at different depths below the reference surface are defined in the reference surface, each of said flats defining a test surface, each said test surface being separated from a next adjacent test surface by a bar having an upwardly facing flat surface disposed at the height of said reference surface.

2. A gauge according to claim 1 wherein the flats are arranged in a sequence of increasing depth.

3. A gauge according to claim 1 in which the sequence of flats extends in a straight line.

4. A gauge according to claim 1 in which the flats are rectangular.

5. A gauge according to claim 1 having at least one channel formed in the reference surface to a depth greater than that of the deepest flat, an edge portion of each of the flats opening into the channel.

6. A gauge according to claim 5 in which there are two such channels with the flats disposed between them.

7. A gauge according to claim 1 in which there is an indicium on or adjacent each flat.

8. A gauge according to claim 7 in which the indicium appears on the reference surface adjacent each flat.

9. A gauge according to claim 7 in which the indicium is located on a surface not contacted in use by the spreader blade.

10. A gauge according to claim 9 in which the indicium is located on a surface which slopes away from the reference surface.

11. Apparatus for determining the fineness of particles suspended in a liquid, comprising:
    means providing an upwardly-facing flat reference surface having a reference height, said reference surface extending along a given length;
    means providing a series of upwardly-facing flat test surfaces parallel to and of progressively decreasing depth relative to said reference surface and arranged in succession alongside said length, each said test surface in said series being separated from each respectively preceding and succeeding test surface in said series by a bar having a upwardly facing flat surface disposed at said reference height;
    a series of indicia applied on said apparatus and denoting respective ones of said test surfaces; and
    a straight-edged spreader blade for sliding along said reference surface while disposed in succession over said test surface, whereby a load of liquid medium containing suspended particles may be loaded upon one of said test surfaces other than the least deep one thereof and spread as a film along upon said series of test surfaces toward said least deep test surface and the first break in said film taken as an indication of translation of particles along the respective test surface due to engagement with the spreader blade.

* * * * *